United States Patent [19]

Knodle

[11] 4,446,869

[45] May 8, 1984

[54] WATER ABSORBING TRAP TO PROTECT AN INFRARED EXHALED CARBON DIOXIDE APNEA MONITOR OF A PATIENT'S RESPIRATION

[75] Inventor: Daniel W. Knodle, Seattle, Wash.

[73] Assignee: Trimed, Inc., Bellevue, Wash.

[21] Appl. No.: 472,722

[22] Filed: Mar. 7, 1983

[51] Int. Cl.³ .................... A61B 5/08; A61M 16/00
[52] U.S. Cl. .................... 128/716; 128/719; 128/207.18; 128/205.12; 137/172; 137/199; 55/387
[58] Field of Search ............... 128/716–730, 128/205.24, 205.12, 205.27, 205.29, 204.18, 205.23, 204.21, 204.23, 207.18, 207.14; 137/197, 199, 172; 55/387

[56] References Cited

U.S. PATENT DOCUMENTS

| 2,326,925 | 8/1943 | Bortini | 128/726 |
| 2,702,089 | 2/1955 | Engelder | 128/205.27 |
| 2,823,693 | 2/1958 | Balter | 137/197 |
| 2,823,694 | 2/1958 | Champion | 137/197 |
| 3,000,191 | 9/1961 | Stark | 55/387 |
| 4,197,858 | 4/1980 | Osborn | 128/718 |

Primary Examiner—Henry J. Recla
Attorney, Agent, or Firm—Roy E. Mattern, Jr.

[57] ABSTRACT

A water trap is connected to a cannula which has a substantially constant internal diameter and which communicates moisture laden patient exhalations therethrough to an analyzer. The trap includes a body having a recess adapted for receiving a water absorbing compound which has an aperture therethrough for communicating dried exhalations to the analyzer. A second recess in the body is adapted for receiving another water adsorbing compound which similarly has an aperture of same diameter. When the first compound becomes substantially saturated and thereby permits moisture laden exhalations to pass therethrough, then the second compound absorbs those exhalations and swells for thereby closing its aperture and preventing communication of moisture laden exhalations to the analyzer.

20 Claims, 7 Drawing Figures

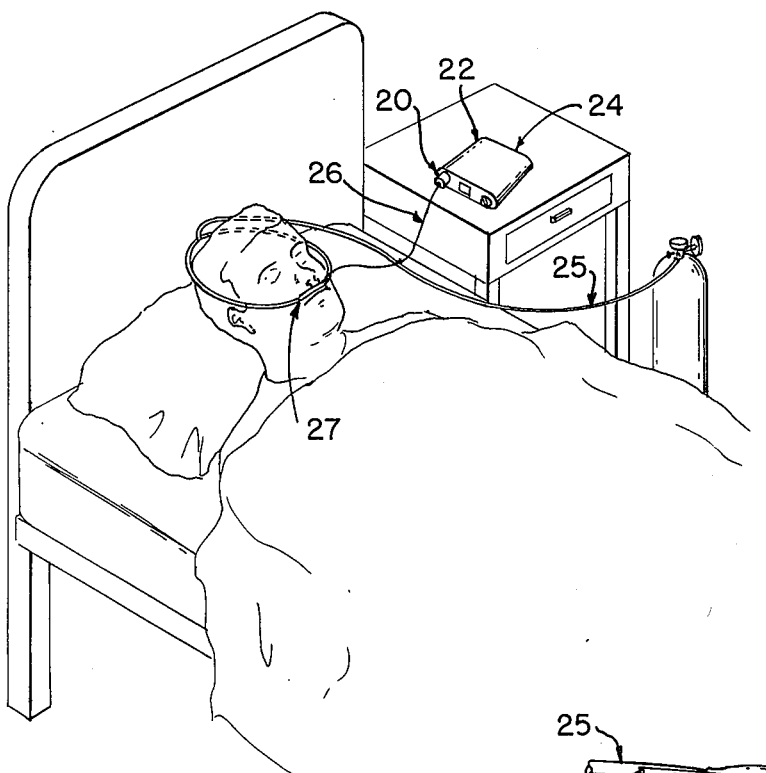
FIG. 1
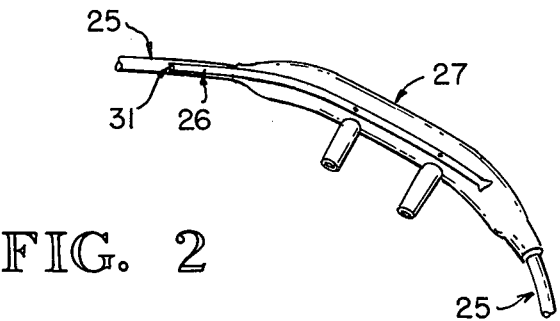
FIG. 2
FIG. 3
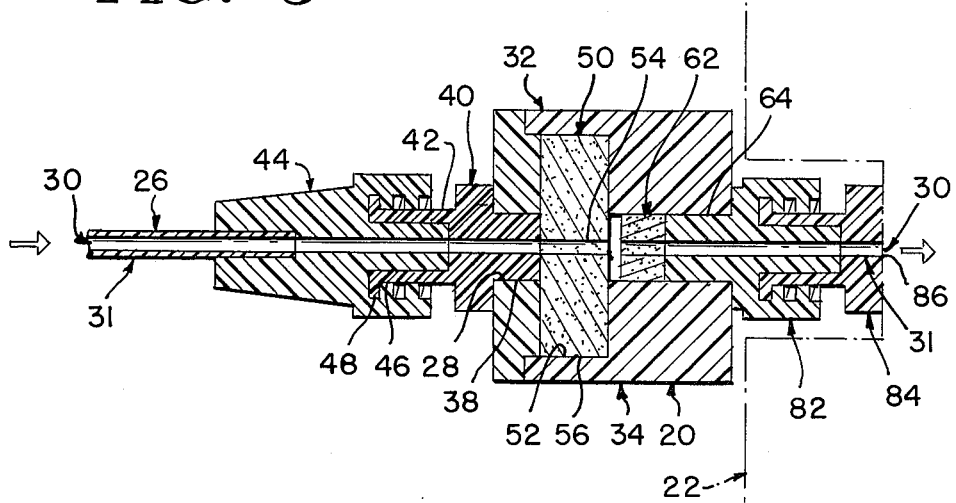

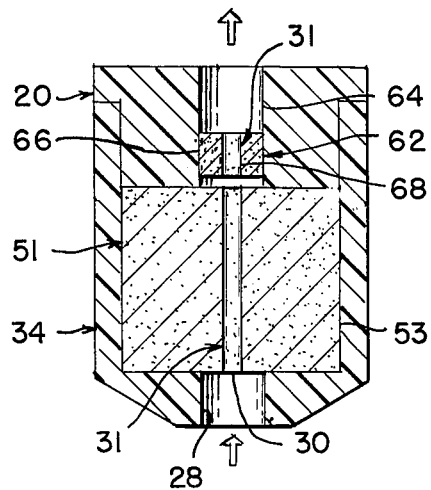
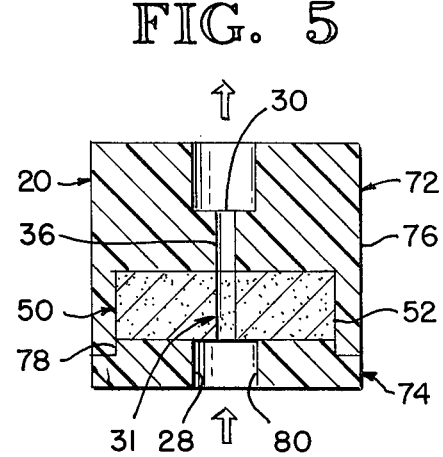
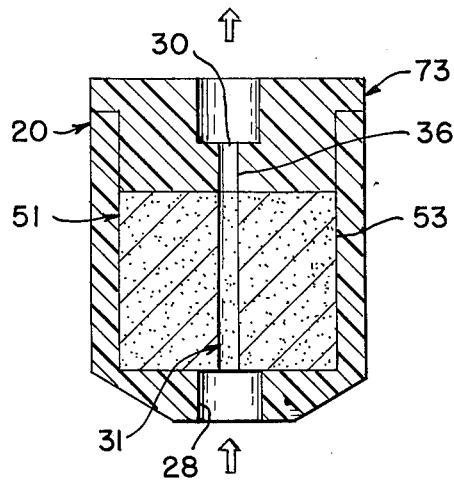
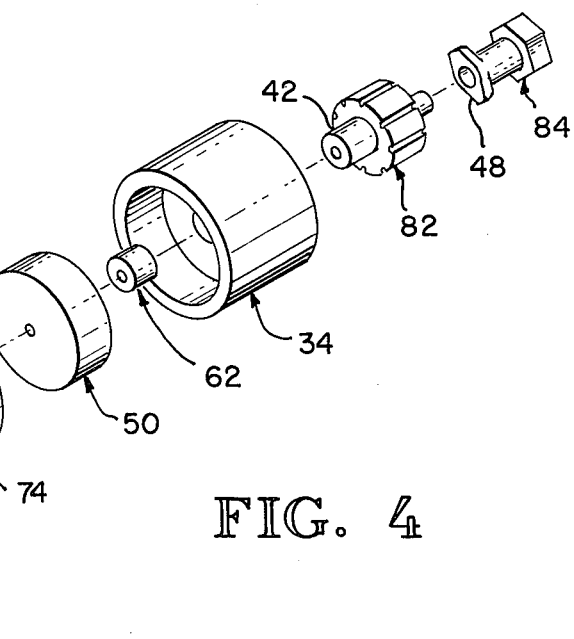
FIG. 6
FIG. 5
FIG. 7
FIG. 4

WATER ABSORBING TRAP TO PROTECT AN INFRARED EXHALED CARBON DIOXIDE APNEA MONITOR OF A PATIENT'S RESPIRATION

BACKGROUND OF THE INVENTION

As set forth in 1980 in John J. Osborn's U.S. Pat. 4,197,858, entitled Sensing Liquid Trap for Respiratory Gas Analyzing Systems, he said, although reliable and rapid response carbon dioxide gas meters for respiratory measurements have been developed for more than twenty-five years, such meters have not been widely used for respiratory monitoring. Yet the continuous measurement of respiratory $CO_2$ concentration is very useful in the care of critical patients undergoing anesthesia, or on mechanical respirators. He further said the non use was based on the impracticability of any moisture or water traps in their collecting of water, before the water or moisture could reach the $CO_2$ gas analyzer, on a continuous basis and without degrading the signal capabilities of the $CO_2$ gas analyzer. He then illustrated and described his sensing, liquid trap made of plastic in an upright hollow cylindrical shape in which the patient's breaths enter downwardly, and after a flow directional change, to eliminate water, the drier breaths flow upwardly, enroute, via a shutoff valve, to the $CO_2$ gas analyzer. When Mr. Osborn's liquid trap, using the fluidic separation process, fills with water, a sensing circuit operates to shut off the valve, thereby protecting the $CO_2$ gas analyzer.

Mr. Richard A. Cronenberg, in 1982, in his U.S. Dept. No. 4,327,718, entitled, Continuously draining Trap for Removal of Condensate From a Patient Breathing Circuit, illustrates how his trap and a trap, like Mr. Osborne's, are positioned between a patient and their respective breathing apparatus.

As indicated by the disclosures of the water traps of Messrs. Osborn and Cronenberg, there remained a need for a very effective small water trap to be closely secured adjacent a respiration monitor, with both being very resistant to damage, when used together in critical areas of hospitals and for portable applications in harsh environments as found by paramedics, and during their use the excellent monitoring of the respiration of a critical patient would be successfully undertaken.

SUMMARY OF THE INVENTION

A very effective, relatively low cost, small water absorbing trap is compactly and protectively arranged for attachment to a rugged, shock resistant comparatively small infrared exhaled carbon dioxide apnea monitor. As so positioned adjacent the apnea monitor and then attached to an end of a sampling cannula, in turn positioned at the opposite end in the nares of a critical patient, this water absorbing trap has a hydrophyllic polymer arranged about a passageway of like diameter to the inside diameter of the cannula, to effectively absorb water or moisture from the passing breaths of the critical patient, so no moisture or water will enter the apnea monitor, and also the adequate analysis of the carbon dioxide of the breaths of the patients will not be impaired.

In a preferred embodiment, within a surrounding molded and/or machined body or housing, a hydrophyllic polymer is placed, such as a high density polyethylene preexpanded to a porosity of 30 microns and pretreated to be hydrophyllic. This polymer has a 0.8" diameter, a 0.2" thickness along the passageway, and a 0.04" center hole serving to continue the overall passageway. After a relatively long operational time of absorbing water, if water is no longer being absorbed by this hydrophyllic polymer, then preferably a hydrophyllic pellet made of cross-linked polymer of polyvinyl pyrrolidone, spaced 0.05" away downstream, intercepts the unabsorbed water and quickly saturates sufficiently to expand and to thereby close its own 0.04" passageway originally matching the internal diameter of the sampling cannula. The water is then compltely stopped and kept from entering the apnea monitor, which thereafter quickly, by sound and sight indications alarms the doctos, nurses, and/or paramedics, in the same way such sound and sight indications would alarm them, when a critical patient had stopped breathing. A preferred embodiment of an expandable hydrophyllic pellet has a 0.2" diameter, a 0.1" thickness, and a 0.04" diameter passageway. The pellet is initially protected from moisture carried in vapors by a thin film, which does not, however, later protect it from water.

DRAWINGS OF THE PREFERRED EMBODIMENTS

A preferred embodiment of the water absorbing trap to protect an infrared absorption exhaled carbon dioxide apnea monitor of a critical patient's respiration is illustrated in the drawings, wherein:

FIG. 1 is an isometric view illustrating the in use positioning of this water absorbing trap secured adjacent to the infrared exhaled carbon dioxide apnea monitor, and the sampling cannula extending from a nose adapter positioned at the nares of a critical patient to the a water absorbing trap, as the patient is receiving oxygen through another large diameter cannula;

FIG. 2 is an enlarged isometric view of a nose adapter or nares fitting for an oxygen cannula of oxygen equipment, provided with extra fittings to receive a smaller cannula, which conducts the patient's exhaled breaths to the water trap and on to the apnea monitor;

FIG. 3 is a cross section of a water absorbing trap, installed between the sampling cannula and the apnea monitor, utilizing both a hydrophyllic polymer to absorb the water and moisture from the breaths of the critical patient, and a downstream hydrophyllic pellet to quickly saturate with water and thereby to expand and shut off the passage of water to the apnea monitor if the hydrophyllic polymer completely fills with water;

FIG. 4 is an exploded isometric view of the water absorbing trap previously shown assembled in FIG. 3, with its connections to the sample cannula and the apnea monitor;

FIG. 5 is a cross section of another water absorbing trap similar to the water absorbing trap illustrated in FIGS. 3 and 4, not having however, the downstream hydrophyllic pellet;

FIG. 6 is a cross section of another water absorbing trap having a larger water absorbing hydrophyllic polymer and a downstream hydrophyllic shutoff pellet; and FIG. 7 is a cross section of another absorbing trap having a larger water absorbing hydrophyllic polymer, but not having a downstream hydrophyllic shutoff pellet.

DESCRIPTION OF THE PREFERRED EMBODIMENTS

Preferred Positioning of the Water Absorbing Trap to Protect the Apnea Monitor Selected embodiments of a water absorbing trap 20, as illustrated in FIGS. 1 and 3 through 7, are particularly suitable for adjacent securement to an infrared exhaled carbon dioxide apnea monitor 22, making this overall combination 24 a very compact and strong respiration monitor assembly 24 for utilization in critical areas of a hospital and for portable applications in harsh environments found by paramedics. By using a cannula 26 conveniently extended from a nose adapter 27 positioned at the nares of a critical patient to the entry 28 of the water absorbing trap 20 located adjacent to the apnea monitor 22, the combination 24 of the water trap 20 and monitor 22, are readily and quickly placed in a convenient location nearby the critical patient during their necessary operating period.

Constant Diameter of Exhaled Respiration Passageway

In all embodiments the cross sectional area 30 of the exhaled respiration passageway 31, defined by the internal diameter of the sampling cannula 26, is maintained to keep the frequency response level of the apnea monitor 22 as high as possible. Therefore, as illustrated in FIGS. 2 and 4, the first embodiment 32 of the water absorbing trap 20, has a surrounding body or housing 34 which has a minimum internal diameter 36 equalling the internal diameter of the cannula 26, thereby maintaining the cross section area 30.

Utilization of Standard Cannulae and Associated Standard Fittings

Standard cannulae and associated standard fittings are used to make connections to and from the water absorbing trap 20 and on to the apnea monitor 22. These standard fittings are already used in other medical applications and they are known in reference to one of the sources as Luer fittings. At the entry end of all the embodiments of the water absorbing trap 20, the respective entries 28 are enlarged to receive a hollow insertable end 38 of a receiving adaptor 40. It is formed at its opposite end 42 to removably but firmly receive a standard end fitting 44 of cannula 26, by utilizing a central hollow insertable end 46 equipped with partial circular flange portions 48. They are threaded onto the threaded interior 49 of the standard end fitting 44.

A Water Absorbing Polymer is Positioned and Protected Within the Housing of the Water Absorbing Trap Soon after entry into these embodiments of the water absorbing trap 20, such as the embodiment 32, a water absorbing polymer 50 is placed in an internal recess 52 of the body 34 and formed with a center passageway 54 maintaining the cross section area 30 of the exhaled respiration passageway 31. The surrounding hollow cylinder 56 of the water absorbing polymer 50 is selectively sized to absorb water and moisture from the exhaled breaths of the critical patient. Also in respect to such sizing the thickness of this hollow cylinder 56 must be large enough to create a sufficiently long enough passageway surface area 58 to initially and to continuously absorb all the moisture and water from the passing exhaled breaths during the specified operational times associated with the selected capacity of each water absorbing polymer 50.

A Preferred Water Absorbing Polymer Material

A high density polyethylene first expanded to a porosity of 30 microns and then treated to be hydrophyllic is a preferred water absorbing polymer material 50 for placement within the internal recess 52 of the body or housing 34 of this water absorbing trap 20.

The Utilization of an Automatic Shutoff of the Flow of Exhaled Breaths Centering on the Use of a Second Polymer, Which Upon Contact with Water Swells to Close Up the Exhaled Respiration Passageway.

As illustrated in FIGS. 3 and 4, in the first embodiment 32 of the water absorbing trap 20 or in the embodiment shown in FIG. 6, to provide for the time when the water absorbing shutoff of the flow of exhaled breaths will occur before they reach the apnea monitor 22, thereby avoiding the entry of moisture and water into its interior. Such unwanted entry of moisture and water tends to downgrade the signals produced, often cancelling them and completely disrupting the operation of the apnea optical infrared absorption sensing of the exhaled carbon dioxide contained in the critical patient's breaths.

This automatic shutoff of the flow of exhaled breaths centers on the use of a second polymer 62, which upon contact with water swells, but does not dissolve, to close up the exhaled respiration passageway 31. As shown in FIGS. 3 and 6 the body or housing 34 has a second smaller internal recess 64 located immediately adjacent to the first internal recess 52, to receive and position this second polymer 62 at a slightly spaced distance downstream. The second polymer 62 is formed as a hollow cylinder 66 having a centered passageway 68 matching the cross section area 30 of the exhaled respiration passageway 31. It is sized to sufficiently expand and block off this passageway 31, thereby protecting the apnea monitor. However, until the water absorbing polymer 50 or 51 is completely filled, this spaced apart pellet shaped shutoff second polymer 62 will not activate, because sufficient water and moisture must reach it before it will expand and block the exhaled respiration passageway 31.

A Preferred Elongating, Swelling or Expanding Polymer Material Activated by Water A cross linked pyrrolidone, after formation into a pellet 62, is covered with a coating of a humidity insensitive material, such as a film of 90% polyvinyl pyrrolidone, which is not cross linked, and a 10% aryl-sulfonamide formaldehyde resin. After the water absorbing polymer 50 is filled, and then water passes on to contact this shutoff pellet 62, this coating dissolves and the molecular chain of this polymer 62 elongates and the overall swelling action places sufficient portions of expanding pelletized polymer 62 across the cross section area 30 of the exhaled respiration passageway 31. The centered passageway 68 of the second polymer 62 is thereby self filled and there no longer is any open sampling conduit 31. In making this pellet 62 of polymer, the coating material selected reduces the sensitivity of the cross link polyvinyl pyrrolidone to humidity, but it does not hinder the swelling of this polymer when it is wetted. Moreover, although the pellet of polymer 62 expands upon being wetted it remains insoluble in water. Therefore, it is not pulled along the sampling conduit 31, thereby effectively maintaining the intended automatic blocking of the exhaled respiration passageway 31, so no moisture laden exhaled breath samples will reach the interior of the apnea monitor 22.

Selected Sizes of the First and Second Polymers

In the illustrated preferred embodiments the first water absorbing polymer shown in FIGS. 3, 4 and 5, in one specific embodiment, has a 0.8" diameter, 0.2" thickness, and a 0.04" diameter center passageway. This selected diameter is not critical but is sized in respect to the specified amount of water to be absorbed during the planned maximum operating periods and at a flow rate of 250 cc per minute. The selection of the 0.2" thickness is somewhat critical for this thickness dimension determines the internal surface area 58 of the water absorbing polymer 50 that is exposed to the exhaled breaths of the critical patient, sometimes referred to as the gas stream. This surface area 58 has to have sufficient path length to fully contact and absorb the water as it tries to pass by at this flow rate of 250 cc per minute. The 0.04" diameter of the center passageway 54, sometimes referred to as the hole 54, is the same diameter as the inside diameter of the cannula 26, sometimes referred to as the sample tube, sampling conduit, or exhaled respiration passageway 31.

The second polymer 62 serving as the automatic shutoff pellet 62 has a 0.04" diameter hole to continue to ensure the integrity of the gas stream until the exhaled breaths are to be automatically or intentionally shut off. By having a 0.2" diameter and a 0.1" thickness sufficient crossed linked polymer is available in the shutoff pellet 62 to swell and thereby shut off the 0.04" diameter exhaled respiration passageway 31 and protect the apnea monitor 22.

As noted previously the above selected sizes are based on a patient's breath flow rate of 250 cc per minute. As the thickness increases, the frequency response realized in the apnea monitor 22 decreases. Therefore generally, in respect to the lower breathing capacities of infants and small children, the first water absorbing polymer 62 has the smaller thickness as shown in FIGS. 3, 4 and 5, whereas in respect to the higher breathing capacities of adults, the polymer 63 has the larger thickness as shown in FIGS. 6 and 7.

Current Sources of Polymers

The water and moisture absorbing high density polyethylene selected to serve as the water absorbing polymer 50 after being treated to the hydrophyllic is preferred to be expanded to each a porosity of 30 microns. At this porosity the water collection is maximized while the diffusion of the carbon dioxide into this absorption media 50 is minimized. Moreover, the signals forthcoming from the apnea monitor 22, as the optical sensing of the exhaled carbon dioxide continues, based on infrared absorption closely compare with the signals that would be forthcoming if the water absorbing trap 20 were to be bypassed.

As described previously the thickness of the polymers 62 or 63 effects frequency responses in the apnea monitor 22. Also the frequency response is effected in reference to the porosity of the polymers 62 or 63. As the porosity increases to 50 microns, the signal slightly becomes less effective. The same decrease is noted in stages as the porosity changes to 90 microns and 125 microns. However, as porosity increases the water capacity goes up, therefore a lowered frequency response could be selectedto provide a greater water absorbing capacity of the polymers 62 or 63.

A current source of hydrophyllic treated polyethylene, is sold under the trademark of INTERFLO, by the Chromex Chemical Corporation of Brooklyn, N.Y. It is available in porosities ranging from 0.8 to 120 microns. Preferably, in reference to the water absorbing polymer 50 positioned in the water absorbing trap 20, the preferred porosities range from 25 to 50 microns. In this range, enough water and moisture absorption capacity is provided while at the same time the carbon dioxide signal is not substantially affected.

The expandable hydrophyllic polymer serving as the second polymer or automatic shutoff pellet 62, is a cross linked polymer of polyvinyl pyrrolidone. Such an expandable polymer is sold under the trademark POLYPLASDONE XL, from G.A.F. Corporation.

Other Embodiments of a Water Absorbing Trap

Other ways, not shown, may be used to timely shut off the exhaled respiration passageway 31, when the water absorbing trap 20 is filled. If so, then other embodiments 72 and 73 of water absorbing traps 20 are provided, as illustrated in FIGS. 5 and 7. There is no second recess 64 because a shutoff pellet 62 is not used.

In the embodiments shown in FIGS. 3, 4 and 5, the smaller water absorbing polymer 50 is illustrated, which although it fills with water in a shorter time period, the signals being monitored are better, especially when the patients are babies and small children. In the embodiments shown in FIGS. 6 and 7, the larger water absorbing polymer 51 is illustrated, which fills with water over a longer time period, however the signals being monitored may be somewhat less distinct.

The water absorbing traps 20 in all embodiments will be produced at sufficiently lower costs, so they will be considered expendable. In some production procedures the water absorbing polymers 50 and 51 wll be inserted into the respective recesses 52 or 53 and thereafter an end encompassing disc 74 is fitted on the body 34 or 76. It is positioned by using its integral inserted portion 78. Also there is centered passageway 80 in this disc 74 to form the entry 28 which receives the insertable end 38 of the receiving adaptor 40.

The Standard Luer Type Connections Used to Secure the Water Absorbing Trap to the Apnea Monitor In FIGS. 3 and 4 in a cross sectional view and in an exploded view, the water absorbing trap 20 is illustrated in respect to its connection to the apnea monitor 22. A receiving unit 84 is provided on the apnea monitor 22, centered about the entry 86 of the exhaled respiration passageway 31, as this passageway 31 continues into the apnea monitor 22. An interconnect unit 82 is threaded on the receiving unit 84. Thereafter the body 34 of the water absorbing trap 20 firmly interfits with this interconnect unit 82.

When so arranged and connected, or similarly arranged and connected, with this apnea monitor 22, the water absorbing trap 20 is immune to the typical monitoring problems of motion artifact, cardiac activity artifact, electrode placement and sensitivity changes, otherwise known to be commonly associated with impedance pneumography monitoring. The overall assemblies are affordable, light weight, and reliable, to be efficiently and effectively utilized by doctors, nurses, paramedics, and others, who are providing excellent care to a critical patient.

I claim:

1. A water trap in combination with a cannula means having a substantially constant pre-selected internal diameter communicating moisture laden patient exhalations to an analyzer, comprising:
   (a) a body having a recess with a diameter in excess of said pre-selected diameter and with a pre-selected volume;
   (b) inlet adaptor means connected to said body and including an aperture in fluid communication with said recess;
   (c) said cannula means having a first end adapted to receive patient exhalations and a second end, said inlet adaptor means secured to said second end of said cannula means and for maintaining said second end internal diameter constant while secured;
   (d) said aperture coaxial with said second end when secured to said inlet adaptor means and having a diameter equal to said pre-selected diameter;
   (e) water absorbent means disposed in said recess and including an aperture therethrough coaxial with said inlet adaptor means aperture and having a diameter equal to said pre-selected diameter;
   (f) said water absorbent means having a volume substantially equal to said pre-selected volume and adapted for drying exhalations;
   (g) exit means connected to said body and including an aperture coaxial with and in fluid communication with said water absorbent means aperture; and,
   (h) an analyzer connected to said exit means, said exit means adapted for communicating dryed exhalations from said body to said analyzer.

2. A water trap as defined in claim 1, further comprising:
   (a) a second recess having a pre-selected volume disposed in said body coaxial with said recess and having a diameter in excess of said pre-selected diameter;
   (b) said second recess positioned intermediate said recess and said exit means and in fluid communication therewith;
   (c) water activated absorbing means disposed in said second recess and including an aperture therethrough coaxial with said water absorbent means aperture and having a diameter equal to said pre-selected diameter;
   (d) said water activated absorbing means having a volume substantially equal to said second recess pre-selected volume; and,
   (e) said water activated absorbing means adapted for rapidly swelling when contacted by water for closing said water activated absorbing means aperture and thereby prohibiting moisture laden exhalations to be communicated therethrough to said exit means whereby substantially complete filling of said water absorbent means causes moisture laden exhalations to be communicated therethrough into contact with said water activated absorbing means.

3. A water trap as defined in claim 2, wherein:
   (a) said water activated absorbing means is a cross linked polyvinyl pyrrolidone.

4. A water trap as defined in claim 2, wherein:
   (a) said water activated absorbing means is not water soluble.

5. A water trap as defined in claim 2, wherein:
   (a) said water activated absorbing means is a cross linked polymer having a humidity insensitive coating.

6. A water trap as defined in claim 2, wherein:
   (a) said coating consisting essentially of approximately 90% by weight polyvinyl pyrrolidone and approximately 10% by weight aryl-sulfonamide formaldehyde resin.

7. A water trap as defined in claim 2, wherein:
   (a) said water activated absorbing means having a critical mass determined by the expanded mass necessary to completely close said water activated absorbing means aperture.

8. A water trap as defined in claim 1, wherein:
   (a) said water absorbent means is a high density polyethylene expanded to a sufficient porosity and treated to be hydrophyllic.

9. A water trap as defined in claim 1, wherein:
   (a) said water absorbent means having a minimum critical thickness along the direction of said water absorbent means aperture determined by said water absorbent means aperture surface area needed for collectively absorbing water from said exhalations.

10. A water absorbing system for patient exhalation analyzers, comprising:
    (a) an analyzer;
    (b) water trap means connected to said analyzer;
    (c) cannula means having a first end adapted for receiving exhalations of a patient and a second end in fluid communication with said water trap means and said analyzer thereby, said cannula means first end adapted for being secured to said patient in a position for receiving exhalations;
    (d) said cannula means having a constant internal diameter;
    (e) said water trap means including a body having a recess with an internal diameter in excess of said cannula means internal diameter and with a pre-selected volume;
    (f) inlet adaptor means connected to said body in fluid communication with said recess for securing said second end of said cannula means to said water trap means and for maintaining said cannula means second end internal diameter constant, said inlet adaptor means having an internal diameter coaxial with and equal to said cannula means second end internal diameter;
    (g) water absorbent means positioned in said recess and having an aperture therethrough coaxial with and having a constant internal diameter equal to said inlet means internal diameter for drying exhalations by absorbing moisture therein, said water absorbent means having a volume substantially equal to said recess volume; and,
    (h) exit means in fluid communication with said water absorbent means aperture and said analyzer for communicating dried exhalations to said analyzer and having an internal diameter coaxial with and equal to said water absorbent means aperture internal diameter.

11. The system as defined in claim 10, further comprising:
    (a) a second recess disposed in said body intermediate said recess and said exit means and having a pre-selected volume;
    (b) said second recess coaxial with said recess and said exit means and in fluid communication therewith;
    (c) water activated absorbing means disposed in said second recess and including an aperture therethrough coaxial with said water absorbent means aperture and having a diameter equal to said water absorbent means aperture diameter;

(d) said water activated absorbing means having a volume substantially equal to said second recess volume; and, (e) said water activated absorbing means adapted for rapidly swelling when contacted by water to thereby close said water activated absorbing means aperture for prohibiting moisture laden exhalations to be communicated therethrough to said analyzer whereby substantially complete filling of said water absorbent means causes moisture laden exhalations to be communicated therethrough into contact with said water activated absorbing means.

12. The system as defined in claim 11, wherein:
(a) said water activated absorbing means is a cross linked polyvinyl pyrrolidone.

13. The system as defined in claim 11, wherein:
(a) said water activated absorbing means is a cross linked polymer coated with a humidity insensitive material.

14. The system as defined in claim 13, wherein:
(a) said humidity insensitive coating consists essentially of approximately 90% by weight polyvinyl pyrrolidone and approximately 10% aryl-sulfonamide formaldehyde resin.

15. The system as defined in claim 11, wherein:
(a) said water activated aborbing means having a critical mass determined by the expanded means necessary to completely close said water activated absorbing means aperture.

16. A water trap as defined in claim 2 or 11, wherein:
(a) said recess diameter exceeds said second recess diameter; and, (b) said recess volume exceeds said second recess volume.

17. The system as defined in claim 10, wherein:
(a) said water absorbent means is a high density polyethylene expanded to a sufficient porosity and treated to be hydrophyllic.

18. The system as defined in claim 10, wherein:
(a) said water absorbent means having a minimum critical thickness along the direction of said water absorbent means aperture determined by said water absorbent means aperture surface area needed for collectively absorbing water from said exhalations.

19. The system as defined in claim 10, wherein:
(a) said first end of said cannula means adapted for being positioned within a nose adaptor.

20. A method of protecting an apnea monitor from the entry of water condensed from the exhaled breaths of critical patients passing through a cannula, so the apnea monitor optically sensing exhaled carbon dioxide via infrared absorption will not be diminished or stopped in its signal rendering capacity, comprising the steps of:

(a) passing the water and exhaled breaths by the sufficient surface of a water absorbing polymer to absorb all the water during a specified operating time of the apnea monitor; and (b) also passing the exhaled breaths, leaving the water absorbing polymer, by a sufficient surface and volume of a second polymer, which, if ever water passes through the water absorbing polymer, will become quickly saturated with water to block the passage of exhaled breaths and water so they will not enter the apnea monitor.

* * * * *